(12) United States Patent
Krämer

(10) Patent No.: US 6,484,595 B1
(45) Date of Patent: Nov. 26, 2002

(54) DEVICE FOR DETERMINING THE DISINTEGRATION TIME OF COMPRESSED PHARMACEUTICAL MOLD BODIES, SUCH AS TABLETS AND CAPSULES, AS WELL AS A METHOD FOR THIS PURPOSE

(76) Inventor: Norbert Krämer, Röntgenstrasse 68, D-64291 Darmstadt (DE)

( * ) Notice: Subject to any disclaimer, the term of this patent is extended or adjusted under 35 U.S.C. 154(b) by 0 days.

(21) Appl. No.: 09/436,922

(22) Filed: Nov. 8, 1999

Related U.S. Application Data

(63) Continuation-in-part of application No. PCT/DE98/01282, filed on May 7, 1998.

(30) Foreign Application Priority Data

May 7, 1997 (DE) .......................................... 197 19 201

(51) Int. Cl.$^7$ .............................................. G01N 33/15
(52) U.S. Cl. ...................................................... 73/866
(58) Field of Search .......................... 73/866; 324/207.2, 324/207.24

(56) References Cited

U.S. PATENT DOCUMENTS 3,618,395 A    11/1971   Melliger

FOREIGN PATENT DOCUMENTS

| CH | 536494  | 4/1973  |
|----|---------|---------|
| DE | 3414507 | 10/1985 |
| DE | 3520034 | 5/1986  |
| DE | 9419245 | 1/1995  |
| WO | 9714035 | 4/1997  |

*Primary Examiner*—Robert Raevis
(74) *Attorney, Agent, or Firm*—Horst M. Kasper

(57) ABSTRACT

An apparatus for determining a disintegration time of compressed pharmaceutical mold bodies includes a vessel filled with a liquid, a frame lowerable into the vessel filled with the liquid, a center column attached to the frame, a floor attached to the center column, wherein the floor contains a plurality of holes, a grid covering the holes from below, a test tube disposed upright and positioned in one of the holes, a disk having passing through holes and movably insertable into the test tube as a weight onto an individual pharmaceutical form body, wherein the passing through holes are running parallel to the direction of the center axis of the disk. A permanent magnet is disposed centered within the disk and has a magnetic field directed axially, wherein the center hole of the disk exhibits a bore hole starting from a lower cover face of the disk, wherein the permanent magnet is seated in the bore hole, wherein the permanent magnet exhibits a permanent magnet hole centeredly in the direction of a center axis, which permanent magnet hole is aligned with the center hole within the disk.

17 Claims, 3 Drawing Sheets

DEVICE FOR DETERMINING THE DISINTEGRATION TIME OF COMPRESSED PHARMACEUTICAL MOLD BODIES, SUCH AS TABLETS AND CAPSULES, AS WELL AS A METHOD FOR THIS PURPOSE

CROSS-REFERENCE TO RELATED APPLICATIONS

This application is a continuation-in-part application of another international application filed under the Patent Cooperation treaty May 7, 1998, bearing Application No. PCT/DE98/01282, and listing the United States as a designated and/or elected country. The entire disclosure of this latter application, including the drawings thereof, is hereby incorporated in this application as if fully set forth herein.

BACKGROUND OF THE INVENTION

1. Field of the Invention

The present invention relates to a device for determining the disintegration time of compressed pharmaceutical mold bodies, such as tablets and capsules, comprising a frame which can be lowered into a vessel filled with a liquid, having a center column and a floor including a plurality of bore holes, wherein the bore holes are covered from below with a sieve and wherein test tubes in upright position are disposed within the frame, wherein in each case a disk with holes passing through the disk in the direction of the center axis can be movably brought in into the test tube as a weight onto individual pharmaceutical mold bodies, wherein a permanent magnet is disposed at the lower side of the disk directed toward the floor, wherein in each case a magnetic field sensor element is disposed below the grid of the floor, as well as a method for this purpose.

2. Brief Description of the Background of the Invention Including Prior Art

The disintegration time measurement of compressed pharmaceutical mold bodies, such as tablets and capsules, is performed according to a standardized test arrangement in order to assure the reproducibility of the measurement results, in particular according to Deutsches Arzneibuch, DAB 10, 3. Supplement 1994 or Europaeisches Arzneibuch or USP (USA). It is determined by the disintegration test, if the tablets or capsules disintegrate in a liquid medium within the pre-scribed time under precisely performed conditions. The main part of the apparatus comprises a rigid frame, which contains six cylindrical test tubes made of glass. Each test tube is furnished with a cylindrical disk made of a transparent plastic material of a precisely pre-scribed relative density and size, which exhibits 5 bore holes passing through, wherein one of the bore holes is led through the center axis of the disk. The test tubes are supported in a vertical position by an upper transparent plate made of plastic material and by a lower transparent plate made of plastic material, wherein the transparent plates in each case have six bore holes. All bore holes have the same distance from the center point and the same distance from each other. A sieve made of stainless steel wire is disposed at the bottom side of the lower plate. A metal column is disposed in the middle of the plates such that the apparatus can be hanged at the metal column in a hanging device and can be moved upward and downward by way of a motor uniformly 28 to 32 times each minute over 50 to 60 mm. For this purpose the apparatus is hanged in a suitable vessel, wherein the vessel contains the pre-scribed liquid. After the filling in of a tablet or capsule into each tube and placing the disk as a weight, then the determination of the dissolution time of the tablets or capsules is performed by observation of the measurement device and taking of the time of the disintegration time by an operating person.

A disintegration apparatus for test bodies, in particular tablets has become known from the German patent DE 3520034 C1, wherein the test bodies are disposed in containers of the disintegration basket between a Hall generator and a disk furnished with a magnet. The containers of the disintegration basket are heated to a constant temperature with a heating means. When the test body disintegrates, then the disk moves together with the magnet toward the Hall generator, such that the Hall generator delivers a signal, which is led to a registration apparatus after the surpassing of a switching threshold and can be displayed. The transfer of the energy for electrical switching circuits in a disintegration basket is performed through contacts or through a high frequency emitter and high frequency receiver. The transfer of the signals to the registration apparatus is performed by optoelectrical components.

An automatic disintegration time measurement apparatus for the pharmaceutical quality control and production control of tablets and sugar-coated pills within a conducting test liquid is known from the German printed patent document DE 9419245 U1, which disintegration time measurement apparatus comprises a basket like frame disposed in a beaker glass with a plurality of glass tubes disposed in the basket like frame, wherein the floors of the glass tubes are formed by circular sieve plates as stand faces for the glass tubes, wherein each sieve plate comprises two wire grid halves being flown through by current and forming electrodes, wherein the wire grid halves are disposed at a distance and are thereby forming a slot. A test sample is disposed in each glass tube, wherein the test sample is covered by a float, and wherein the float rests on the test sample. The float exhibits on the bottom side an embedded contact frame made of a metallic material. Upon motion of the beaker glass and the disintegration of the tablets, the conductivity of the test fluid changes, wherein the conductivity can be measured between the wire grid halves and the contact frame of the float.

A tablet disintegration time measurement apparatus with moving small tubes in a bath liquid is known from U.S. Pat. No. 3,618,295 having a multitude of electrodes disposed opposite to each other at a distance on the floor of the small tubes containing the tablets. The presence of a tablet interferes with an electromagnetic field applied at the electrodes, wherein the interference influences a time clock, wherein the signals of the time clock can be evaluated.

A device for determining the disintegration time of compressed pharmaceutical mold bodies has become known from the World Intellectual Property Organization publication WO 97/14035, wherein an electric coil is disposed at the floor of the frame around each hole, wherein the electrical coil is part of an electrical oscillating circuit, wherein a conductor loop is disposed on the disk for a path depending damping of the electrical oscillating circuit, wherein the electrical oscillating circuit and the conductor loop are jointly connected to an electrical evaluation device for oscillation generation and evaluation of the measurement results. The coil can be formed as an insertion coil, a single layer coil, or as a multiple layer coil.

Conventional steps for fully automatic measurement started on the one hand always with impermissible changes of the test apparatus, wherein such changes however are permissible only in a very small range according to Deutsches Arzneibuch DAB 10. On the other hand the device according to the last recited document WO 97/14035 delivers relatively precise measurement results, however requires an extensive electronic expenditure in the signal generation and signal evaluation.

SUMMARY OF THE INVENTION

Purposes of the Invention

It is an object of the present invention to furnish a device of the kind initially recited, which captures contactless the motion of the disks within the device and without larger changes of the pre-scribed parameters for the apparatus according to Deutsches Arzneibuch DAB 10 and which is to determine continuously the decreasing thickness of compressed pharmaceutical mold bodies during the dissolution process.

It is another object of the present invention to furnish a device which reliably and precisely measures a disintegration behavior of a tablet or capsule.

BRIEF DESCRIPTION OF THE INVENTION

The present invention provides that the central hole of the disk exhibits centeredly a bore starting at the lower cover face of the disk, where a permanent magnet is seated in the bore, wherein the permanent magnet exhibits centeredly a bore hole in the direction of the center axis, wherein the bore hole is aligned with the central bore within the disk, wherein the magnetic field sensor element is disposed in the region of the peripheral edge of the cover face of the permanent magnet in the region of the largest gradient of the magnetic field of the permanent magnet as seen in a top planar view.

Usually the residual thickness of a pharmaceutical mold body is a pre-given set point value. If the actual value of the pharmaceutical mold body is the residual thickness, then the pharmaceutical mold body is deemed to be dissolved.

Advantageously the apparatus is constructed such that the geometry and the thickness of the disks employed as well as the geometry of the test tubes and the construction of the sieve floor of the frame remains unchanged. Similarly the disks and the frames are exchangeable amongst each other, without that a re-calibration of the apparatus has to be performed. In particular such disks can be employed, which exhibit according to the prescription also five holes, wherein one of the five holes is a centered middle hole. The disks are only constructed such that a permanent magnet with a hole is disposed within this disk around the centered middle bore, such that the central bore of the disk is continued by the hole of the permanent magnet. The sleight addition in weight by the permanent magnet can be balanced in a simple way by insertion of small hollow spaces into the disk, such that the pre-scribed weight of the disk is maintained.

Advantageously, the permanent magnet is formed cylindrical and of tubular or sleeve shape, wherein the longitudinal extension of the permanent magnet is larger than the diameter of the permanent magnet. This way the magnetic stray of the permanent magnet can be maintained small. The permanent magnet is completely surrounded of plastic material within the disk, for example a plastic sleeve is inserted into the hole of the permanent magnet.

The magnetic field sensor element can be a Hall generator or a magneto-resistive sensor or a saturable core probe, wherein a Hall generator is preferred, where the Hall generator is capable of measuring even smallest changes in field strength.

The magnetic field sensor element or, respectively, the Hall generator is disposed in the region of the largest gradient of the magnetic field, as soon as the permanent magnet stands directly opposed to the magnetic field sensor element in the final position of the disk. For this reason it is advantageous that the main part of the sensor with small dimensions is disposed so far spaced apart that the main part of the sensor with small dimensions is disposed immediately below the annular front face of the magnet, that is in a top planar view sideways to the hole of the permanent magnet.

Furthermore each channel is measured several times during a disintegration process with the apparatus and an average value formed from the measurements. It is also possible to scan each of the six magnetic field sensor elements by way of a fast multiplexer.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1A:
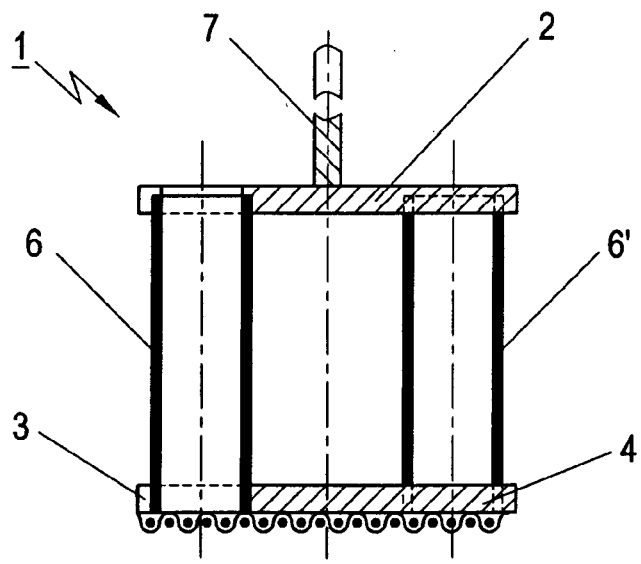
FIG. 1a is a schematic side elevational view and in part sectional view of a frame of a state of the art construction according to the DAB 10.
Figure 1B:
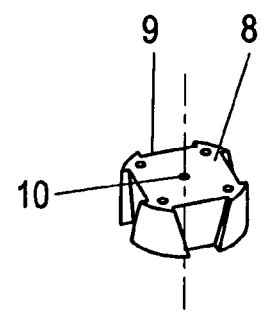
FIG. 1b is a schematic top planar view of a frame of a state of the art construction according to the DAB 10.
Figure 1C:
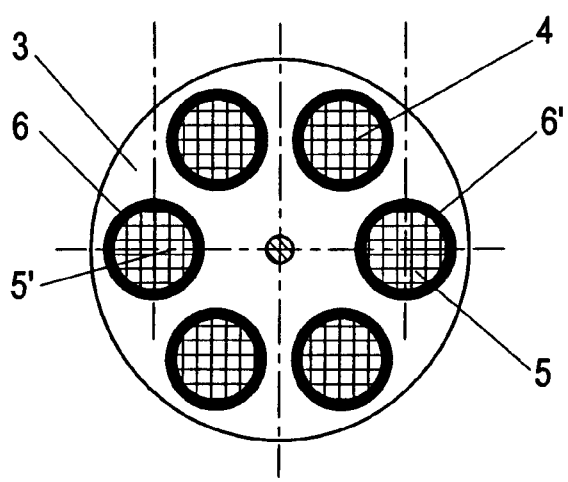
FIG. 1c is a schematic perspective view of a disk of a state of the art construction according to the DAB 10.

The FIGS. 1a, 1b, and 1c show an apparatus according to the German Arzneibuch DAB 10, 3. Supplement 1994, as it is employed according to the present invention. The apparatus comprises a frame 1 with a center column 7 as well as a circular cover plate 2 and of floor 3, which exhibit a plurality of holes 5, 5', usually six, wherein the test tubes 6, 6', made of glass are disposed. The floor 3 is covered at the bottom side with a sieve made of stainless steel wire. The plates 2, 3 are held apart from each other by vertical metal rods not illustrated and disposed at the outer side of the frame 1. In each case a tablet or capsule is placed into each test tube 6, 6'for testing disintegration, and a disk, which is furnished with precisely defined recesses 9 as well as four to five bore holes 10, 10', which disk is placed onto the tablet or capsule as a weight and the disintegration time is measured. Advantageously the disk 8 is furnished with a centered bore hole 10, wherein the bore hole 10 runs along the middle axis of the disk 8.

PREFERRED EMBODIMENT OF THE INVENTION

Figure 2:
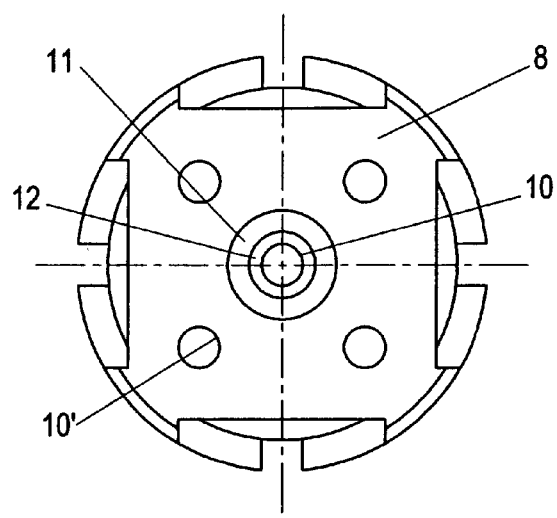
FIG. 2 is a top planar view of the disk, as the disk is placed and inserted into each test tube, wherein the disk contains a sleeve shaped magnet.

A disk according to the present invention is shown in FIG. 2, wherein the disk is formed similarly to the disk in FIG. 1b.

The 1994 Supplement to the DAB 10 defines dimensions of a disk on page 1 and 2 of V.5.1.1 and these are preferred dimensions as far as applicable of the disk 8. The disk 8 can have a largest diameter of from about 20 to 22 millimeters with a preferred value of 20.7 millimeters. The disk 8 can have a thickness of from about 9 to 10 millimeters with a preferred value of 9.5 millimeters. The holes can have an open diameter of from about 1 to 3 millimeters with a preferred value of 2 millimeters. The distance from the central hole in the disk 8 to one of the peripheral holes in the disk 8 can be from about 5 to 7 millimeters and is preferably 6 millimeters. The diameter peripheral hole in the disk 8 to an oppositely disposed peripheral hole in the disk 8 can be from about 10 to 14 millimeters and is preferably 12 millimeters. Once a plastic sleeve is inserted into the hole of the permanent magnet 11, then the open inner diameter of the plastic sleeve is preferably 2 millimeters and the outer diameter of the plastic sleeve can be from about 3 millimeters to 5 millimeters. A preferred embodiment of the plastic sleeve has an outer diameter of 2 millimeters and a wall thickness of 0.5 millimeters.

The permanent magnet 11 can exhibit an inner diameter of from about 3 to 5 millimeters and preferably of up to about 4 millimeters and an outer diameter from about 6 millimeters to 9 millimeters. The permanent magnet 11 can exhibit a length of from about 2 to 8 millimeters. A preferred embodiment of the permanent magnet 11 exhibits a length of 7.5 millimeters, an outer diameter of 6 millimeters, and an inner diameter of 3 millimeters. Another preferred embodiment of the permanent magnet 11 exhibits a length of about 7 millimeters, an outer diameter of about 7 millimeters, and an inner diameter of 3.7 millimeters.

The permanent magnet is made of a material having a high remanence, for example a ferrite magnet with a remanence of preferably more than 300 millitesla and more preferably about 500 millitesla. Alternatively permanent magnets made of rare earth materials such as SmCo can exhibit a remanance of about 1 tesla. A preferred permanent magnet 11 is made of a neodymium-iron-boron alloy NeFeB having a remanance of about 1.2 tesla. In addition it is commendable to employ a material for the permanent magnet which has a high magnetic permeability. For example, N-30 H is suitable as a magnet material.

Alternatively to employing a plastic sleeve 12, the permanent magnet 11 can either partly or completely be covered by a stainless plastic lacquer or varnish. In case the permanent magnet 11 is covered by a plastic lacquer or varnish, then the film of lacquer or varnish can be very thin and the inner diameter of the permanent magnet 11 can approach down to about 2 millimeters. If the permanent magnet 11 is not enclosed by plastic material (FIG. 3), then the permanent magnet 11 is covered with a protecting lacquer layer at least at positions, where it is exposed outside of the material of the disk 8.

The difference of the present disk to the disk in FIG. 1a comprises that the disk 8 of FIG. 2 along the centered axis exhibits a permanent magnet 11 wherein the permanent magnet 11 is furnished with a hole 25 (FIG. 5) and is thus formed of an annular shape, which hole 25 also expands in the direction of the centered axis of the disk 8 or, respectively, in the direction of the centered axis 27 (FIG. 5) of the permanent magnet 11. The permanent magnet 11 is completely embedded into the material of the disk 8 and surrounded by the material of the disk 8 and in fact preferably starting from the larger bottom side of the disk 8, as can be gathered from FIG. 3. For this purpose, the center hole 10 of the disk 8 exhibits a bore hole 28 centeredly starting from the lower cover face of the disk 8, where the permanent magnet 11 is seated in the bore hole 28, which permanent magnet 11 exhibits the hole 25 centered in the direction of the middle axis 27, which hole 25 is aligned with the central hole 10 within the disk 8, wherein the magnetic field sensor element 13 is disposed on the permanent magnet 11 in the region of the peripheral edge of the cover face of the permanent magnet 11 as seen in a top planar view in the region of the largest gradient of the magnetic field of the permanent magnet 11.

The permanent magnet 11 can be preferably disposed near the upper cover face of the disk 8 or near the lower cover face of disk 8.

A plastic tube or plastic sleeve 12 (FIG. 2) is inserted into the hole 25 of the permanent magnet 11, which hole 25 can be a bore hole, wherein the plastic tube 12 extends beyond the length of the permanent magnet and reaches up to the upper edge of the upper surface of the disk 8. The plastic sleeve 12 has an inner cylindrical surface 101 having an inner diameter to meet the requirements of a disk 8 of a standard testing device. The lower front face of the permanent magnet 11 is also covered with a thin plastic coating, such that the permanent magnet 11 is completely embedded disposed in this way within the disk 8 and completely surrounded by plastic.

Figure 3:
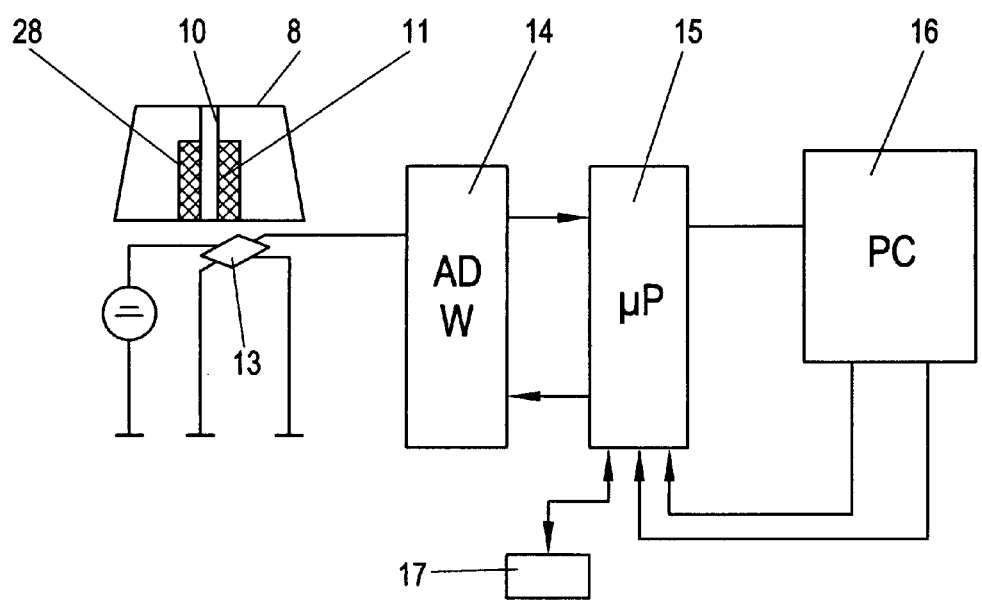
FIG. 3 is a side elevational view of the embodiment of FIG. 2 with the arrangement of the Hall generator as well as of the following electronic evaluation circuit for the measurement signals.
Figure 5:
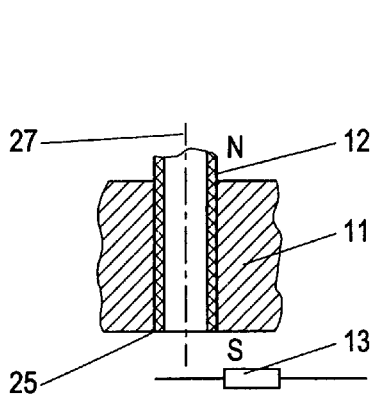
FIG. 5 is an enlarged view illustrating the permanent magnet and the arrangement of the magnetic sensor at the peripheral edge of the lower front face of the permanent magnet.

The permanent magnet 11 is preferably tubular shaped or sleeve shaped cylindrically formed according to FIGS. 3 and 5, wherein the longitudinal extension of the permanent magnet 11 is larger than the diameter of the permanent magnet 11. It is accomplished in this way that the permanent magnet 11 at its poles N-S forms a magnetic field with a strong gradient in the immediate region of the front faces.

The tubular shape of the permanent magnet 11 allows that the disk 8 of the present invention is compatible to the requirements according to Deutsches Arzneibuch, DAB 10, 3. Supplement 1994 or Europaeisches Arzneibuch or USP (USA). The tubular shape of the permanent magnet 11 is associated with the advantage that the magnetic field lines are bundled toward the outside of the permanent magnet 11, that is in a more peripheral location as compared with a solid permanent magnet.

Figure 6:
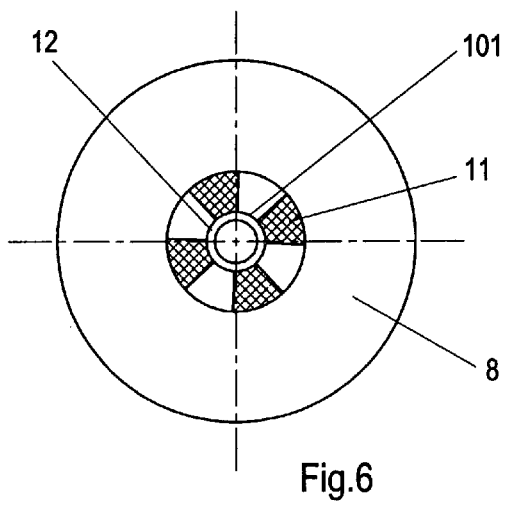
FIG. 6 is a view of a horizontal section through a device according to the invention employing permanent magnet rods of cylinder sector shape.

It is not necessary that the permanent magnet 11 is a fully cylindrical body, but can be substituted by configurations which approximate such a fully cylindrical body. For example, the permanent magnet 11 can be represented by a plurality of rod magnets aligned in parallel and disposed sequentially along a circular line. The polarity of all the rods is parallel directed. The rod permanent magnets can have a rectangular cross-section or a circular cross-section or can be cylinder sectors 111 as shown in FIG. 6.

The magnetic field sensor element is capable to capture also relatively weak magnetic fields in a sufficient way, in particular where the magnetic field sensor element is disposed in the region of the largest gradient of the magnetic field, as soon as the disk 8 together with the permanent magnet 11 has reached the lower end position within the test tube 6. A Hall generator or a magneto-resistive sensor or a saturable core probe can be employed as a magnetic field sensor element. A suitable Hall sensor is represented by the Hall element "KSY14" furnished by Siemens AG having an office in Edison N.J. An alternative Hall element is furnished by the ITT corporation as Hall element "Type 400". Saturable core probes are position sensors out of a special, very small soft magnetic core, wherein the soft magnetic core is unwound by a coil. This coil allows determination of the magnetization state of the sensor core by the permanent magnet with the aid of an external control and evaluation electronics.

The magnetic field sensor employed has to exhibit a high magnetic field sensitivity as well as a small construction height as well as also a control by the permanent magnet, which can very flexibly be adapted to the application.

The magnetic field sensor is preferably disposed at or near the location of the largest gradient of the magnetic field of the permanent magnet 11. The sensor element is preferably disposed such that its measurement direction is aligned with the magnetic field lines. Alternatively, a vertical or horizontal component of the magnetic field strength can be measured. The magnetic field sensor element is preferably disposed in the area of the peripheral edge of the permanent magnet 11 as seen in a top planar view onto the permanent magnet 11. Thus the magnetic field sensor element can be disposed both inside of a vertical projection of the permanent magnet 11 as well as outside of a vertical projection of the permanent magnet 11.

Furthermore, FIG. 3 shows the electrical connection of the magnetic field sensor element 13, which here is presented as a Hall generator 13 with a supply voltage. The Hall generator 13 delivers a voltage to its output, wherein the voltage corresponds to the strength of the magnetic field of the permanent magnet 11 as well as to the distance of the permanent magnet 11 from the Hall generator 13.

Similarly, a magnetic resistor can be employed as a magnetic field sensor element, wherein in this case the output signal is obtained as a voltage drop at the magnetic resistor. The output signal of the Hall generator 13 or, respectively, of the magnetic resistor in each case are fed to an analog/digital converter 14 and from there to a microprocessor 15 and are digitalized. The microprocessor 15 is connected to a computer 16, wherein the disintegration process can be displayed and monitored through the computer.

The microprocessor 15 can cause the analog digital converter 14 to measure the corresponding channel several times for increasing the sensitivity of the measurement. A storage element RAM 17, which is preferably buffered, is furnished for permanent storage of the final values and of the changing thickness of the dissolving pharmaceutical mold body. The disintegration time is determined with the connected computer 16.

Figure 4:
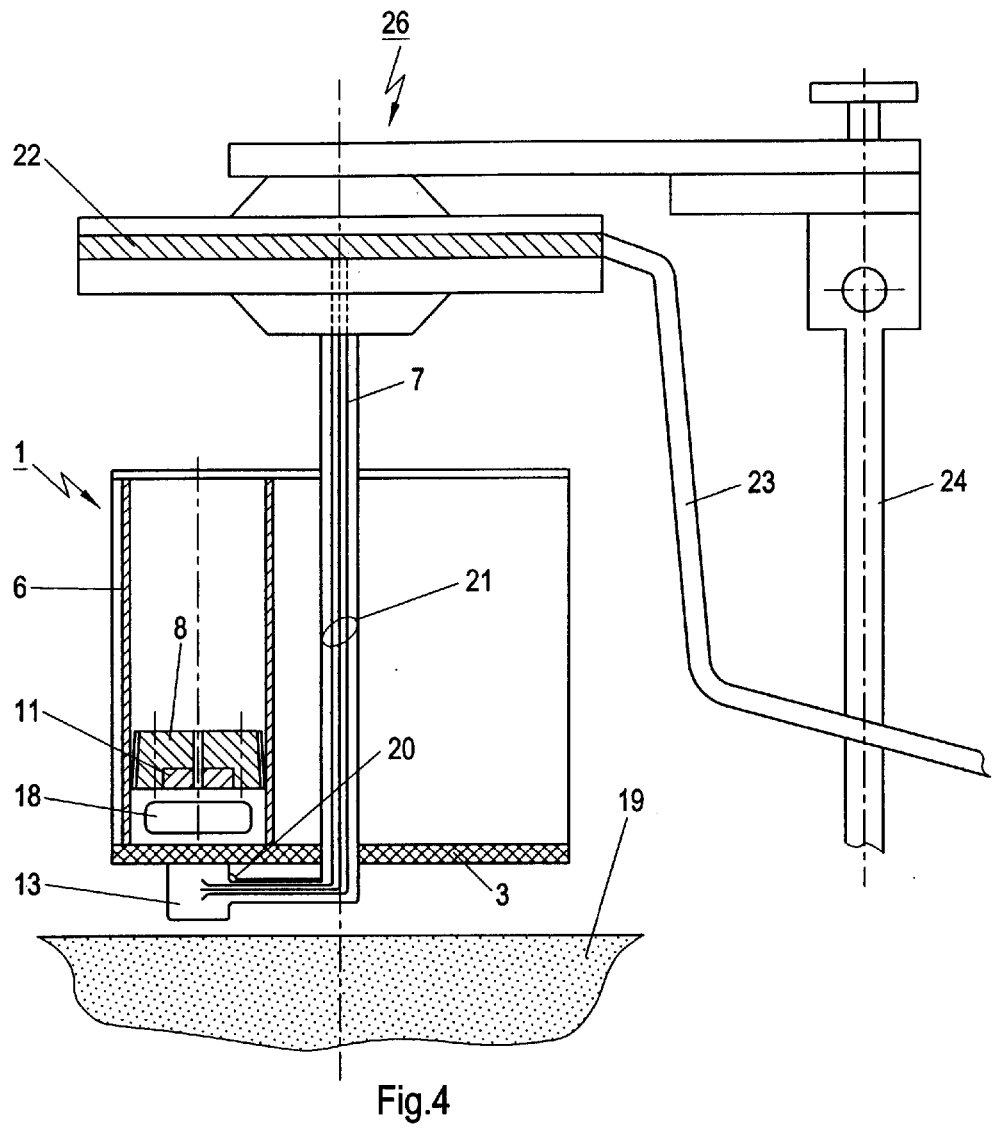
FIG. 4 is a side elevational view of a device according to the present invention, wherein only one of the test tubes is shown.

FIG. 4 shows a side elevational view of the device, wherein only one of the test tubes 6 is shown. The lowerable frame 1 is disposed above a vessel 19, wherein a liquid, preferably water, is disposed in the vessel 19. The pharmaceutical mold body 18 as well as a disk 8 thereabove are disposed within the test tube 6, wherein the disk 8 exhibits a permanent magnet 11. The magnetic field sensor element 13 is disposed below the floor 3, wherein the electrical feed lines 21 of the magnetic field sensor element 13 are led through the center column 7 of the frame 1 and are connected to a circuit board 22, wherein the circuit board 22 is part of the head part 26 of the complete apparatus. The head part 26 is attached at a vertical column 24, wherein the vertical column 24 allows the lowering and the rising of the head part 26 together with a frame 1 into the vessel 19. A cable 23 leads to the computer 16, wherein the computer 16 is shown in FIG. 3.

The measurement process is such that an electrical multiple measurement with a successive average value formation is performed during the dissolution process of the pharmaceutical mold body. Here the changing magnetic field of the permanent magnet 11 depending on the instantaneous distance of the permanent magnet 11 from the magnetic field sensor element 13 as well as the disintegration time or sinking time or only of the disintegration time are measured. The instantaneous value of the magnetic field with a dissolving pharmaceutical mold body is a measure over the instantaneous height of the permanent magnet 11 above the magnetic field sensor element 13 and thus over the instantaneous residual thickness of the pharmaceutical mold body 18. The capturing of the maximum magnetic field is to be set equal to the complete dissolution of the pharmaceutical mold body 18.

Commercial Application:

The subject matter of the invention is suitable as a highly precise and highly sensitive measurement apparatus for the measurement of the disintegration or decay time of pharmaceutical mold bodies according, to the German Arzneibuch DAB 10, 3. Supplement 1994 or the European Arzneibuch or the USP (USA).

It will be understood that each of the elements described above, or two or more together, may also find a useful application in other types of testing systems differing from the types described above.

While the invention has been illustrated and described as embodied in the context of an apparatus for determining the disintegration time of compressed pharmaceutical mold bodies, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Apparatus for determining the disintegration time of compressed pharmaceutical mold bodies (18) comprising a frame (1) immersible into a vessel (19) filled with a liquid, wherein the frame (1) is furnished with a center column (7) and a floor (3), which floor (3) contains a plurality of holes (5,5'), wherein the holes (5,5') are covered from below with a sieve (4) and wherein test tubes (6,6') disposed upright are positioned in the holes (5,5') within the frame (1), wherein a disk (8) with passing through holes (10, 10') is movably insertable as a weight on the individual pharmaceutical form body (18), wherein the holes (10, 10') are running in the direction of the center axis of the disk (8), wherein a permanent magnet (11) is disposed at the bottom side of the disk (8) directed toward the floor (3), wherein a magnetic field sensor element (13) is disposed opposite to the permanent magnet (11) below a grid (4) of the floor (3), wherein the center hole (10) of the disk (8) exhibits a bore hole (28) starting from a lower cover face of the disk (8), wherein the permanent magnet (11) is seated in the bore hole (28), wherein the permanent magnet (11) exhibits a hole (25) centeredly in the direction of the center axis (27), which hole (25) is aligned with a centered hole (10) within the disk (8), wherein the magnetic field sensor element (13) is disposed in the region of the peripheral edge of the cover face of the permanent magnet (11) in the region of the largest gradient of the magnetic field of the permanent magnet (11) when seen in a top view onto the permanent magnet (11).

2. The apparatus according to claim 1, wherein the permanent magnet is disposed at the bottom side of the disk at a location directed toward the floor.

3. The apparatus according to claim 1, wherein the permanent magnet is formed as a sleeve shaped cylindrical torus, and wherein the longitudinal extension of the torus is larger than the diameter of the torus.

4. The apparatus according to claim 1, wherein the permanent magnet is surrounded completely within the disk by plastic material.

5. The apparatus according to claim 1 further comprising a plastic sleeve inserted into the permanent magnet hole of the permanent magnet.

6. The apparatus according to claim 1, wherein the magnetic field sensor element is a member selected from the group consisting of a Hall generator, a magneto-resistive sensor and a saturable core probe.

7. The apparatus according to claim 1, wherein the permanent magnet exhibits an inner diameter of from about 3 to 5 millimeters, an outer diameter from about 6 millimeters to 9 millimeters, and a length of from about 2 to 8 millimeters.

8. The apparatus according to claim 1, wherein the permanent magnet is formed by a plurality of parallel disposed permanent magnet rods aligned with the center axis of the disk on a circle surrounding the center axis.

9. An apparatus for determining a disintegration time of compressed pharmaceutical mold bodies (18) comprising a frame (1) lowerable into a vessel (19) filled with a liquid, wherein the frame (1) is furnished with a center column (7) and a floor (3), which floor (3) contains a plurality of holes (5,5'), wherein the holes (5,5') are covered from below with a grid (4) and wherein test tubes (6,6') disposed upright are positioned in the holes (5,5') within the frame (1), wherein a disk (8) with passing through holes (10, 10') is movably insertable as a weight on the individual pharmaceutical form body (18), wherein the passing through holes (10, 10') are running in the direction of the center axis of the disk (8), wherein a permanent magnet (11) is disposed at the bottom side of the disk (8) directed toward the floor (3), wherein a magnetic field sensor element (13) is disposed opposite to the permanent magnet (11) below a grid (4) of the floor (3), wherein the center hole (10) of the disk (8) exhibits a bore hole (28) starting from a lower cover face of the disk (8), wherein the permanent magnet (11) is seated in the bore hole (28), wherein the permanent magnet (11) exhibits a permanent magnet hole (25) disposed centeredly in the direction of the center axis (27), which permanent magnet hole (25) is aligned with the center hole (10) within the disk (8), wherein the magnetic field sensor element (13) is disposed in the region of a peripheral edge of a cover face of the permanent magnet in a region of a largest gradient of the magnetic field of the permanent magnet (11) when seen in a top view onto the permanent magnet (11).

10. The apparatus according to claim 9, wherein the permanent magnet (11) is formed as a tubular shaped or sleeve shaped cylindrical torus, wherein the longitudinal extension of the torus is larger than the diameter of the torus.

11. The apparatus according to claim 9, wherein the permanent magnet (11) is surrounded completely within the disk (8) by plastic material.

12. The apparatus according to claim 11 wherein a plastic sleeve (12) is inserted into the hole (25) of the permanent magnet (11).

13. The apparatus according to claim 9, wherein the magnetic field sensor element (13) is a Hall generator, or a magneto-resistive sensor or a saturable core probe.

14. A method for determining the disintegration time of compressed pharmaceutical mold bodies comprising the steps of:
employing an apparatus comprising:
a frame lowerable into a liquid;
a center column attached to the frame;
a floor attached to the center column, wherein the floor contains a plurality of holes;
a grid covering the holes from below;
a test tube disposed upright and positioned in one of the holes;
a disk having passing through holes and movably insertable into the test tube as a weight onto an individual pharmaceutical form body, wherein the passing through holes are running parallel to the direction of the center axis of the disk;
a permanent magnet disposed centered within the disk and having a magnetic field directed axially, wherein the center hole (10) of the disk exhibits a bore hole starting from a lower cover face of the disk, wherein the permanent magnet is seated in the bore hole, wherein the permanent magnet exhibits a permanent magnet hole centeredly in the direction of a center axis, which permanent magnet hole is aligned with the center hole within the disk,
a magnetic field sensor element disposed opposite to the permanent magnet below the grid of the floor, wherein the magnetic field sensor element is disposed in the region of a peripheral edge of a cover face of the permanent magnet in a region of a largest gradient of a magnetic field of the permanent magnet when seen in a top view onto the permanent magnet;
placing a medical mold body into the test tube;
disposing the disk on top of the medical mold body;
lowering the frame into the vessel filled with the liquid;
performing an electrical multiple measurement with successive average value formation durning a disintegration process of the medical mold body.

15. An apparatus for determining a disintegration time of compressed pharmaceutical mold bodies comprising
a vessel filled with a liquid;
a frame lowerable into the vessel filled with the liquid;
a center column attached to the frame;
a floor attached to the center column, wherein the floor contains a plurality of holes;
a grid covering the holes from below;
a test tube disposed upright and positioned in one of the holes;
a disk having passing through holes and movably insertable into the test tube as a weight onto an individual pharmaceutical form body, wherein the passing through holes are running parallel to the direction of the center axis of the disk;
a permanent magnet disposed centered within the disk and having a magnetic field directed axially, wherein the center hole of the disk exhibits a bore hole starting from a lower cover face of the disk, wherein the permanent magnet is seated in the bore hole, wherein the permanent magnet exhibits a permanent magnet hole centeredly in the direction of a center axis, which permanent magnet hole is aligned with the center hole within the disk, a magnetic field sensor element disposed opposite to the permanent magnet below the grid of the floor, wherein the magnetic field sensor element is disposed in the region of a peripheral edge of a cover face of the permanent.

16. An apparatus for determining a disintegration time of compressed pharmaceutical mold bodies comprising a frame lowerable into a liquid;

a center column attached to the frame;

a floor attached to the center column, wherein the floor contains a plurality of holes;

a grid covering the holes from below;

a test tube disposed upright and positioned in the holes; a disk having passing through holes and movably insertable into the test tube as a weight onto an individual pharmaceutical form body, wherein the passing through holes are running parallel to the direction of the center axis of the disk;

a permanent magnet disposed centered within the disk and having a magnetic field directed axially, wherein the center hole of the disk exhibits a bore hole starting from a lower cover face of the disk, wherein the permanent magnet is seated in the bore hole, wherein the permanent magnet exhibits a permanent magnet hole centeredly in the direction of a center axis, which permanent magnet hole is aligned with the center hole within the disk, a magnetic field sensor element disposed opposite to the permanent magnet below the grid of the floor, wherein the magnetic field sensor element is disposed in the region of a peripheral edge of a cover face of the permanent magnet in a region of a largest gradient of a magnetic field of the permanent magnet when seen in a top view onto the permanent magnet.

17. An apparatus for determining a disintegration time of compressed pharmaceutical mold bodies (18) comprising a frame (1) lowerable into a liquid, wherein the frame (1) is furnished with a center column (7) and a floor (3), which floor (3) contains a plurality of holes (5,5'), wherein the holes (5,5') are covered from below with a grid (4) and wherein test tubes (6,6') disposed upright are positioned in the holes (5,5') within the frame (1), wherein a disk (8) with passing through holes (10, 10') is movably insertable as a weight on the individual pharmaceutical form body (18), wherein the passing through holes (10, 10') are running in the direction of the center axis of the disk (8), wherein a permanent magnet (11) is disposed at the bottom side of the disk (8) directed toward the floor (3), wherein a magnetic field sensor element (13) is disposed opposite to the permanent magnet (11) below a grid (4) of the floor (3), wherein the center hole (10) of the disk (8) exhibits a bore hole (28) starting from a lower cover face of the disk (8), wherein the permanent magnet (11) is seated in the bore hole (28), wherein the permanent magnet (11) exhibits a permanent magnet hole (25) disposed centeredly in the direction of the center axis (27), which permanent magnet hole (25) is aligned with the center hole (10) within the disk (8), wherein the magnetic field sensor element (13) is disposed in the region of a peripheral edge of a cover face of the permanent magnet in a region of a largest gradient of the magnetic field of the permanent magnet (11) when seen in a top view onto the permanent magnet (11).

* * * * *